United States Patent
Yee

(10) Patent No.: US 7,413,566 B2
(45) Date of Patent: Aug. 19, 2008

(54) TRAINING ENHANCED PSEUDO ACCOMMODATION METHODS, SYSTEMS AND DEVICES FOR MITIGATION OF PRESBYOPIA

(75) Inventor: Kingman Yee, San Jose, CA (US)

(73) Assignee: AMO Manufacturing USA, LLC, Santa Ana, CA (US)

( * ) Notice: Subject to any disclaimer, the term of this patent is extended or adjusted under 35 U.S.C. 154(b) by 411 days.

(21) Appl. No.: 11/134,027

(22) Filed: May 19, 2005

(65) Prior Publication Data

US 2006/0264916 A1 Nov. 23, 2006

(51) Int. Cl.
*A61B 18/20* (2006.01)
(52) U.S. Cl. .................. 606/5; 606/4; 606/10; 128/898
(58) Field of Classification Search .................. 606/4–6, 606/10–12; 607/88, 89; 128/898
See application file for complete search history.

(56) References Cited

U.S. PATENT DOCUMENTS

| | | | | |
|---|---|---|---|---|
| 5,533,997 | A * | 7/1996 | Ruiz | 606/5 |
| 5,682,223 | A | 10/1997 | Menezes et al. | |
| 5,684,560 | A | 11/1997 | Roffman et al. | |
| 5,724,258 | A | 3/1998 | Roffman | |
| 5,807,377 | A | 9/1998 | Madhani et al. | |
| 6,200,342 | B1 | 3/2001 | Tassignon | |
| 6,273,092 | B1 * | 8/2001 | Nolan | 128/898 |
| 6,280,435 | B1 | 8/2001 | Odrich et al. | |
| 6,302,877 | B1 * | 10/2001 | Ruiz | 606/5 |
| 6,497,701 | B2 * | 12/2002 | Shimmick et al. | 606/5 |
| 6,554,429 | B1 | 4/2003 | Campin et al. | |
| 6,679,606 | B2 | 1/2004 | Campin et al. | |
| 6,682,196 | B2 | 1/2004 | Sheets, Jr. et al. | |
| 6,814,729 | B2 * | 11/2004 | Youssefi et al. | 606/10 |
| 6,887,232 | B2 | 5/2005 | Billie et al. | |
| 7,261,412 | B2 * | 8/2007 | Somani et al. | 351/177 |
| 2002/0140902 | A1 | 10/2002 | Guirao et al. | |
| 2002/0167643 | A1 | 11/2002 | Youseffi | |
| 2003/0199858 | A1 | 10/2003 | Schelonka | |
| 2004/0169820 | A1 | 9/2004 | Dai | |

(Continued)

FOREIGN PATENT DOCUMENTS

WO   WO 2004/053568 A1   6/2004

OTHER PUBLICATIONS

Loewenfeld, Irene, E., *The Pupil: Anatomy, Physiology and Clinical Applications*, vol. 1, (© 1993) Wayne State University Press, Detroit, MI, pp. 296, 301-304.

(Continued)

*Primary Examiner*—Ahmed M Farah
(74) *Attorney, Agent, or Firm*—Townsend & Townsend & Crew LLP; Mark D. Barrish

(57) ABSTRACT

Devices, systems, and methods for developing prescriptions for and/or treating presbyopia may use a combination of an alteration to the refractive tissues of the eye with changes in the response of the visual system. The visual system response may include using residual accommodation in a manner similar to that employed by latent hyperopes, a trained response of the pupil, trained psychophysics, or the like. Associated refractive prescriptions may be tailored to take advantage of the subsequent visual system response so as to mitigate presbyopia.

22 Claims, 11 Drawing Sheets

U.S. PATENT DOCUMENTS

2004/0246440 A1  12/2004  Andino et al.
2005/0043717 A1   2/2005  Snow

OTHER PUBLICATIONS

Moreira et al., "Multifocal Corneal Topographic Changes with Excimer Laser Photorefractive Keratectomy" *Arch. Ophthalmol.* (1992) 110:994-999.

Vinciguerra et al., "Excimer Laser Photorefractive Keratectomy for Presbyopia: 24-month Follow-up in Three Eyes" *Journal of Refractive Surgery* (198) 14:31-31.

Holladay et al., "Functional Vision and Corneal Changes After Laser In Site Keratomlleusls Determined By Contrast Sensitivity, Glare Testing, and Corneal Topography", *J. Cataract Refractive Surg.* 1999, vol. 25, No. 5, pp. 663-669.

\* cited by examiner

TRAINING ENHANCED PSEUDO ACCOMMODATION METHODS, SYSTEMS AND DEVICES FOR MITIGATION OF PRESBYOPIA

BACKGROUND OF THE INVENTION

This invention generally relates to optical correction, and in particular provides methods, devices, and systems for mitigating or treating presbyopia and/or other vision conditions. Exemplary embodiments employ aspherical refractive corrections for providing appropriate accommodative power with changes in pupil size.

Presbyopia is a condition that affects the accommodation properties of the eye. As objects move closer to a young, properly functioning eye, the effects of ciliary muscle contraction increases the optical power of the lens of the eye to focus at nearer distances. Hence, accommodation can allow the eye to focus and refocus between near and far objects.

Presbyopia normally develops as a person ages, and is associated with a natural progressive loss of accommodation, sometimes referred to as "old sight." The presbyopic eye often loses the ability to rapidly and easily refocus on objects at varying distances. Although the condition progresses over the lifetime of an individual, the effects of presbyopia usually become noticeable after the age of 45 years. By the age of 65 years, the crystalline lens has often lost most of its elastic properties and has only limited ability to change shape. Residual accommodation refers to the amount of accommodation that remains in the eye. A lower degree of residual accommodation contributes to more severe presbyopia, whereas a higher amount of residual accommodation correlates with less severe presbyopia.

A variety of methods and devices for treatment of presbyopia have been employed, with varying results. The goal of such treatments is generally to allow the eye to see clearly both distant objects and near objects. Reading glasses have traditionally allowed the eye to focus on and maintain a clear image of near objects by adding plus power diopter to the eye, using an approach similar to that applied for treatment of farsightedness or hyperopia. To facilitate viewing both near and far objects, presbyopia has also been treated with bifocal eyeglasses. A variety of other approaches have also been suggested, but none of the known presbyopia-treatment modalities that are commonly used by patients have been shown to be without drawbacks for at least some cases.

In work associated with embodiments of the present invention, it has recently been proposed to provide refractive shapes which take of advantage of changes in a size of a patient's pupil with changes in viewing distances, so as to provide enhanced optical imaging. U.S. patent application Ser. No. 10/738,358 entitled "Presbyopia Correction Using Patient Data," as filed on Dec. 5, 2003, presents a variety of approaches for establishing prescriptions that mitigate or treat presbyopia of particular patients. Suitable shapes may be optically optimized, scaled or otherwise varied, and/or may provide optical powers that change with pupil size, with the preferred prescriptions often being tailored to measurements of a patient's eye at differing viewing conditions. U.S. patent application Ser. No. 10/892,386, as filed on Jul. 14, 2004, and entitled "Correction of Presbyopia Using Adaptive Optics and Associated Methods" describes systems and devices which may be suited for accurately measuring characteristics of the eye at differing viewing distances. Both these references are incorporated herein by reference. By taking advantage of these recent improvements, many patients may experience enhanced abilities to view at different viewing distances without the inconvenience of reading glasses, bifocals, or the like.

While the recent proposals may represent a significant advancement in the art, as with many such successes, still further improvements would be desirable. In particular, work in connection with embodiments of the present invention indicates that the benefits of pseudo accommodation can be limited in at least some cases. Hence, it would be advantageous to provide improved devices, systems, and methods for treatment of presbyopia, and particularly to provide such improvements so as to extend the benefits of the recently proposed presbyopia mitigation techniques to additional individual patients, groups of patients, and the like. It may also be advantageous to increase the clinical efficacy of presbyopia-mitigating techniques so as to improve optical imaging, acuity, and/or patient satisfaction.

BRIEF SUMMARY OF THE INVENTION

The present invention generally provides improved devices, systems, and methods for developing prescriptions for and/or treating one or both eyes of a patient. Embodiments of the invention are particularly well suited for addressing presbyopia, and may help provide improved viewing at differing viewing distances using an alteration to the refractive tissues of the eye, together with changes in the response of the patient's visual system. The visual system response may include, for example, using residual accommodation in a manner similar to that employed by a latent hyperope. A variety of other helpful visual system responses may also be taken advantage of, including a trained response of the pupil, trained psychophysics, or the like. Advantageously, the refractive prescription may be tailored to take advantage of one or more of these visual system imaging stimuli responses. Although full visual response training time may be surprisingly long, so that if training is not started until after a procedure the patient's satisfaction may not peak until significantly after the refractive properties of the eye have stabilized, once a patient's visual response has adapted to a suitable refractive prescription the patient may achieve accuity results of 20/20 vision or better and J3 or better. Refractive prescriptions (along with devices and methods for their generation and/or imposition) are also provided which are particularly well suited to take advantage of the subsequent visual system response so as to mitigate presbyopia for a wide range of patients.

In a first aspect, the invention provides a method for treating presbyopia in a vision system of the patient. The vision system includes an eye, and the method comprises applying a refractive prescriptive change to the eye. The refractive change alters optical properties of the eye so as to provide a first near acuity and a first far acuity. In response to the altered optical properties of the eye, a modified response of the visual system is induced so as to provide a second near acuity which is better than the first near acuity, and/or a second far acuity which is better than the first far acuity, such that presbyopia of the eye is mitigated.

The modified response of the visual system may significantly improve visual acuity from an optically stabilized acuity to a trained acuity. This improvement may occur significantly after the altered optical properties of the eye have substantially stabilized. For example, when the optical properties of the eye are applied using a LASIK procedure, the eye may have substantially stabilized optically in as little as one hour after the procedure. Nonetheless, a significant improvement in near visual acuity may be provided only after more than one hour later than the LASIK procedure, in many cases occurring more than one day after the LASIK procedure, and often occurring more than one week after the LASIK procedure. In some cases, the full benefit of a presbyopia treatment may be provided more than one month after the LASIK procedure, that a patient measured one month after the LASIK procedure can have a first visual acuity when viewing at a near distance, and that same patient may have a significantly improved second near visual acuity when measured still later, such as three months after the LASIK procedure.

A modified response of the visual system will often include a modified tissue response to imaging stimuli. This tissue response may comprise psychophysics, a trained pupil pseudo-accommodation, latent presbyopia-like accommodation, and/or the like. Such visual system responses may be obtained by training the visual system of the patient to take advantage of the altered optical characteristics available after the refractive prescription is applied to the eye. Advantageously, the visual system response may be anticipated, and the refractive prescription may be generated using the anticipated visual system response. The anticipated visual system response may be determined by studying the visual system responses of prior patients, and/or may be determined by measurements of the patient being treated. For example, when a permanent refractive alteration of the patient's eye is planned, temporary refractive alterations (such as contact lenses or the like) may be used in such measurements.

Ideally, the initial far acuity will be at least 20/20, so that the mitigation of presbyopia may be effected by improving near visual acuity after the prescriptive change is imposed. The refractive prescription will often be tailored or determined using a measured response of the eyes of the patient, often by measuring a pupil dilation response, a residual accommodation, or the like. The anticipated visual system response may correspond to a rate of change in total overall effective power of the eye with changes in pupil size, allowing a refractive prescription to be used even though an effective refractive power of the prescription has a rate of change that is lower than the total rate. For example, the refractive prescription may correspond to a change in effective power with changes in pupil size at a rate of between about 0.4 D per millimeter and about 0.6 D per millimeter. After the refractive prescription is imposed, the a change in manifest power with a change in pupil size (which may correspond to the total compensation rate) may be significantly greater than this rate.

In another aspect, the invention provides a system for treating presbyopia in a visual system of a patient. The visual system includes an eye, and the system comprises a laser for resculpting the eye of the patient according to a refractive prescription. The prescription alters optical properties of the eye so that the eye, after optical stabilization, has a first near acuity and first far acuity. A processor is coupled to the laser resculpting system. The processor determines the refractive prescription from optical properties of the eye, such that the optical properties of the eye as altered by the prescription induce a modified response of the visual system. This modified response provides a second near acuity better than the first near acuity, or a second far acuity better than the first far acuity. Hence, presbyopia of the eye is mitigated.

In yet another aspect, the invention provides a system for determining a refractive prescription so as to mitigate presbyopia in a visual system of a patient. The visual system includes an eye with refractive tissue. The system comprises an aberrometer for measuring initial optical properties of the eye, and a processor coupled to the aberrometer. The processor determines the refractive prescription from the initial optical properties of the eye so that the refractive tissues of the eye provide a first near acuity and first far acuity. The altered optical properties of the eye are configured by the processor to induce a modified response of the visual system so as to provide a second near acuity better than the first near acuity, or a second far acuity better than the first far acuity (and in some cases both). Hence, the presbyopia of the eye will be mitigated.

BRIEF DESCRIPTION OF THE DRAWINGS

FIGS. 10A-C schematically illustrate optical properties of an eye at differing pupil sizes.

DETAILED DESCRIPTION OF THE INVENTION

In general, presbyopes have lost a significant amount (but often not all) of the accommodation amplitude typically exhibited by young patients. This reduction in accommodation may be related to a loss of ability to change shape in the lens of the eye. To compensate for the loss in accommodation, it may be desirable to increase the power of the refractive system of the eye when viewing objects at a near distance.

As an eye adjusts from viewing a far object to viewing at a near distance, the near accommodative reflex includes constriction of the pupil at the eye tries to focus on the near target. Embodiments of the present invention may take advantage of this pupil constricting accommodative reflex through use of an aspheric prescriptive lens. Such a prescriptive lens may be employed anterior to the patient's cornea (such as a contact lens, or the like), within the patient's cornea (such as through selective stromal ablation), or posterior of the cornea (such as with an intra-ocular lens "IOL"). Regardless, the aspheric prescriptive lens may, at least in part, mimic the accommodative properties of a healthy eye. For example, as the eye adjusts from viewing at a far viewing distance to a near viewing distance. The prescriptive aspheric lens may take advantage of the constriction of the pupil to increase the power of the refractive tissues in the eye, thereby mimicking, at least to some extent, the change in accommodative power of the eye with changes in pupil size that would occur if the eye were not presbyopic (or were less presbyopic). The desired total change in accommodative power of the eye with changes in pupil size will sometimes be referred to herein as the "accommodative trajectory" of the eye. In may embodiments, the prescriptive aspheric lens to be applied to a particular patient will be derived at least in part from the accommodative trajectory of that specific patient. In other embodiments, the prescriptive shape may be based at least in part on accommodative trajectories of one or more prior patients.

In many embodiments, the accommodative trajectory will be measured by stimulating accommodation of the patient and measuring characteristics of the eye, often including the pupil size. The accommodation stimulus can be at a continuous range of distances from the eye or at individual discreet viewing distances. The range of viewing distance stimuli will preferably encompass a distant target at more than 20 feet viewing distance from the eye, preferably at an effectively infinite viewing distance, and a near viewing target at a viewing distance of less than 16 inches from the eye, ideally with a plurality of intermediate viewing distance targets at viewing distances therebetween.

Figure 1:
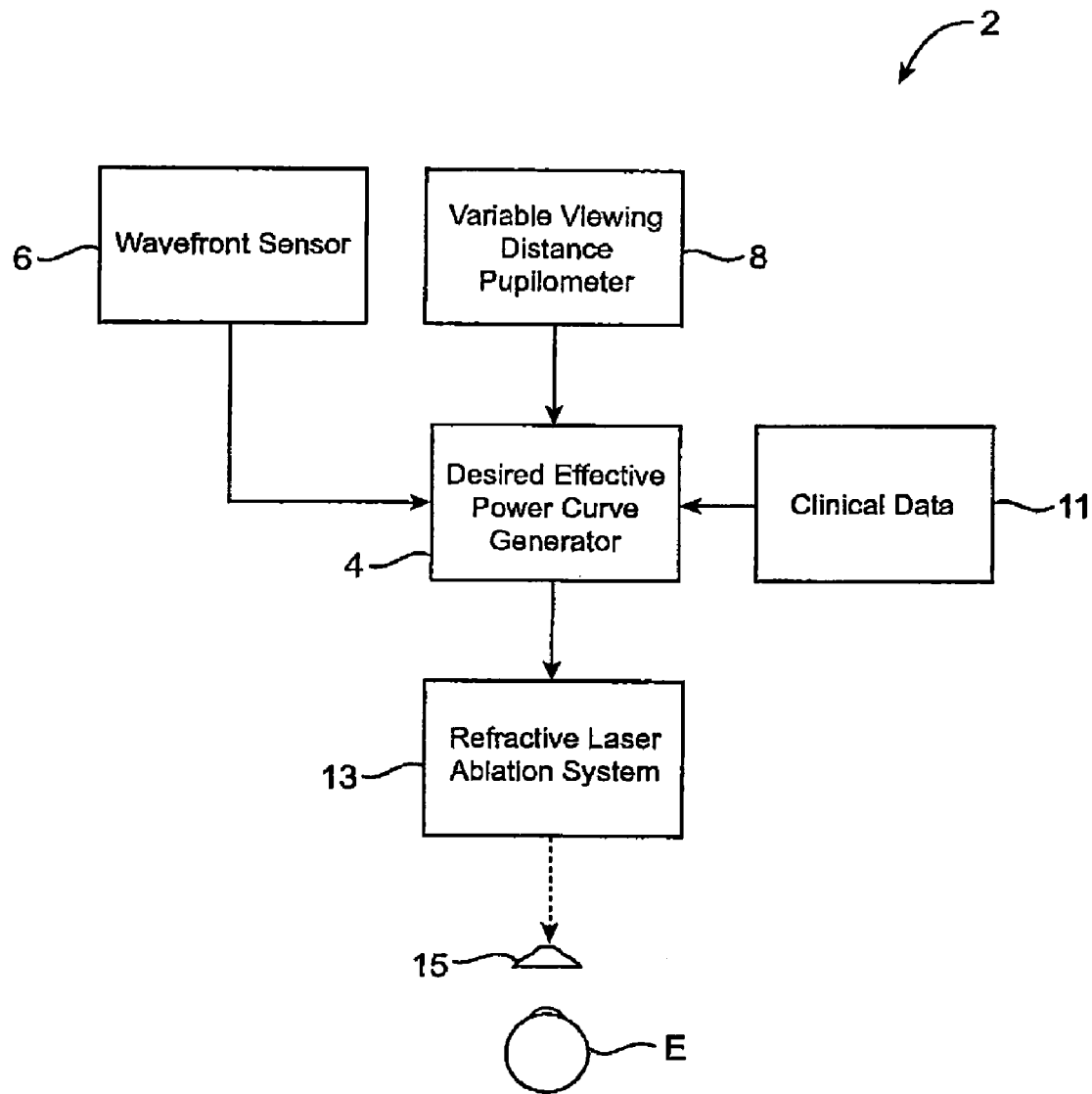
FIG. 1 is a schematic block diagram illustrating a system for generating and imposing a refractive prescription suitable for inducing a response of the visual system so as to mitigate presbyopia.

Referring now to FIG. 1, a presbyopia system 2 is schematically illustrated. Presbyopia system 2 may be used to determine an appropriate prescription for treatment of a patient and/or effect that treatment so that presbyopia is mitigated. For developing an appropriate prescription, presbyopia system 2 generally includes a desired effective power curve generator 4 which makes use of information from a wavefront sensor 6 and/or a variable viewing distance pupilometer 8. In some embodiments, clinical data 11 from one or more prior refractive treatments may be factored into the prescription by desired effective power curve generator 4.

Once an appropriate prescription has been developed, presbyopia system 2 may optionally be used to treat eye E, optionally using a refractive laser ablation system 13. Laser system 13 will often be used to selectively ablate a portion of a cornea of eye E. In some embodiments, laser ablation system 13 may be used to form a lens 15, such as a contact lens, an intraocular lens ("IOL"), or the like. Such a lens may be used to verify that the prescription is appropriate for eye E and that the patient is satisfied with the resulting visual system performance. Laser system 13, or another laser system, may then be used to impose the prescription on the corneal tissue of the eye. In some embodiments, lens 15 may be used to at least begin training the visual system so as to take advantage of the refractive properties of the prescription, or the like.

Eye characteristics such as pupil size, the accommodative trajectory, and/or the like may be measured by variable viewing distance pupilometer 8. Once the accommodative trajectory of the patient's eye is known, the desired effective power curve generator 4 can use this information to determine the desired prescriptive power as a function of pupil size. In some embodiments, an aspheric shape can be designed so as to emulate the full accommodative trajectory power change. In many embodiments, the aspheric shape may not provide all of the power indicated by the accommodative trajectory. For example, the eye may make use of any remaining residual accommodation so as to provide good visual acuity throughout a desired range of viewing distances, ideally providing acuities of 20/25 or better and J3 or better, and in many cases providing acuities of 20/20 or better and J1 or better. Hence, desired effective power curve generator 4 may adjust the prescription so as to take advantage of residual accommodation or the like, rather than attempting to fully compensate for changes in viewing distances using changes in effective power of the refractive prescription alone in at least some cases. Surprisingly, such residual accommodation benefits may not be fully available to at least some eyes until a modified visual response has been induced, such as by training the eye to take advantage of the modified ocular optics.

Figure 2:
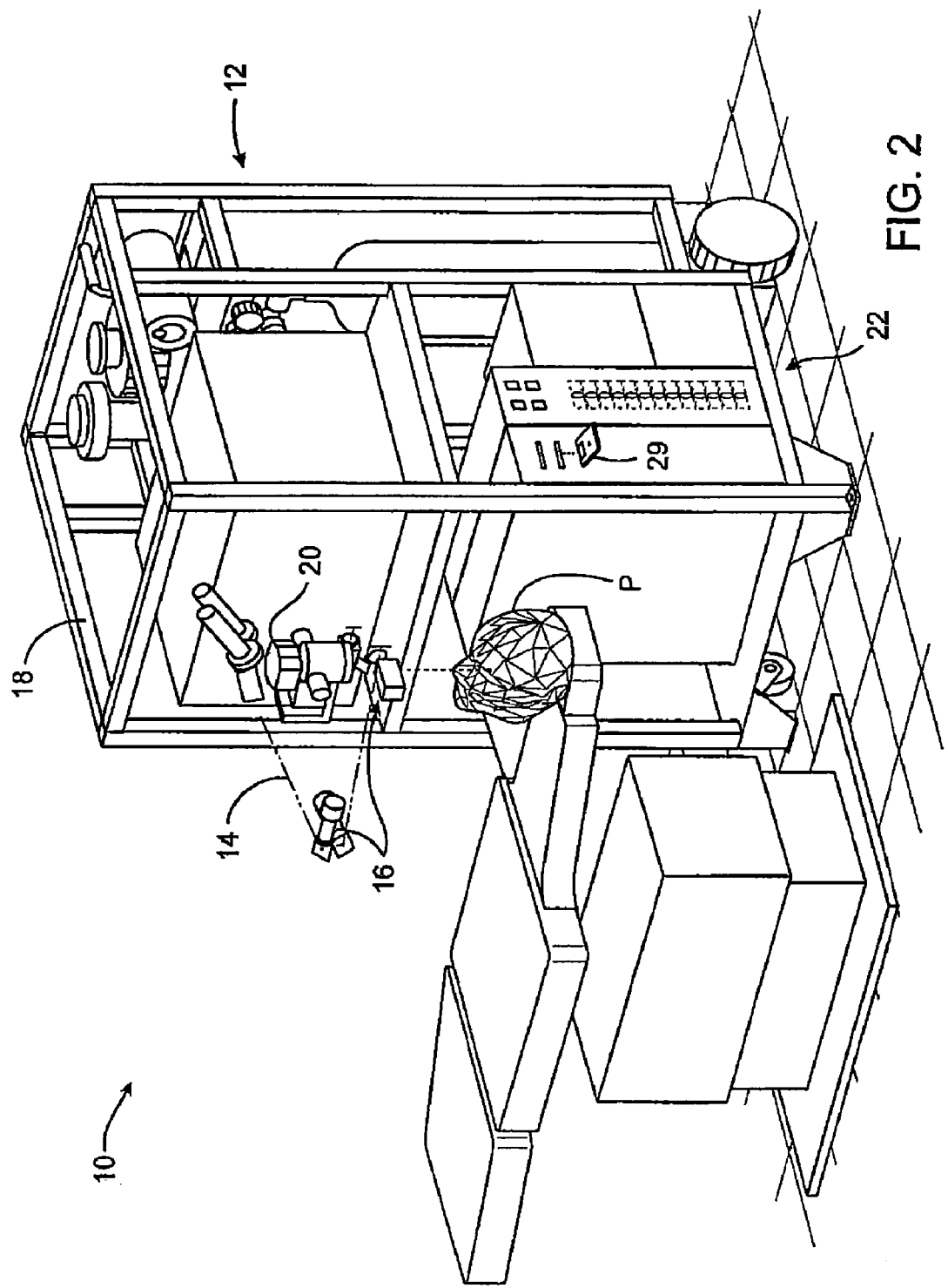
FIG. 2 illustrates a laser eye surgery system for imposing a refractive prescription on a cornea of a patient.

Referring now to FIG. 2, a laser eye surgery system 10 may be used as refractive laser system 13 (see FIG. 1), and includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via laser delivery optics 16. The present invention may also be useful with alternative sources of ultraviolet or infrared radiation, particularly those adapted to controllably ablate the corneal tissue without causing significant damage to adjacent and/or underlying tissues of the eye. In alternate embodiments, the laser beam source employs a solid state laser source having a wavelength between 193 and 215 nm as described in U.S. Pat. Nos. 5,520,679 and 5,144,630 to Lin and U.S. Pat. No. 5,742,626 to Mead, the full disclosures of which are incorporated herein by reference. In another embodiment, the laser source is an infrared laser as described in U.S. Pat. Nos. 5,782,822 and 6,090,102 to Telfair, the full disclosures of which are incorporated herein by reference. Hence, although an excimer laser is the illustrative source of an ablating beam, other lasers may be used in the present invention.

Laser 12 and laser delivery optics 16 will generally direct laser beam 14 to the eye of patient P under the direction of a computer system 22. Computer system 22 may perform some or all of the functions of effective power curve generator 4, or may comprise a separate processor structure. Computer system 22 will also often selectively adjust laser beam 14 to expose portions of the cornea to the pulses of laser energy so as to effect a predetermined sculpting of the cornea and alter the refractive characteristics of the eye. In many embodiments, both laser 12 and the laser delivery optical system 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table, and the treatment table may be adjusted according to feedback input into computer system 22. The laser treatment system 10, and computer system 22 may continue and/or terminate a sculpting treatment in response to the feedback, and may optionally also modify the planned sculpting based at least in part on the feedback.

Additional components and subsystems may be included with laser system 10, as should be understood by those of skill in the art. Further details of suitable systems for performing a laser ablation procedure can be found in commonly assigned U.S. Pat. Nos. 4,665,913; 4,669,466; 4,732,148; 4,770,172; 4,773,414; 5,207,668; 5,108,388; 5,219,343; 5,646,791; and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss Meditec, and the like.

Figure 2A:
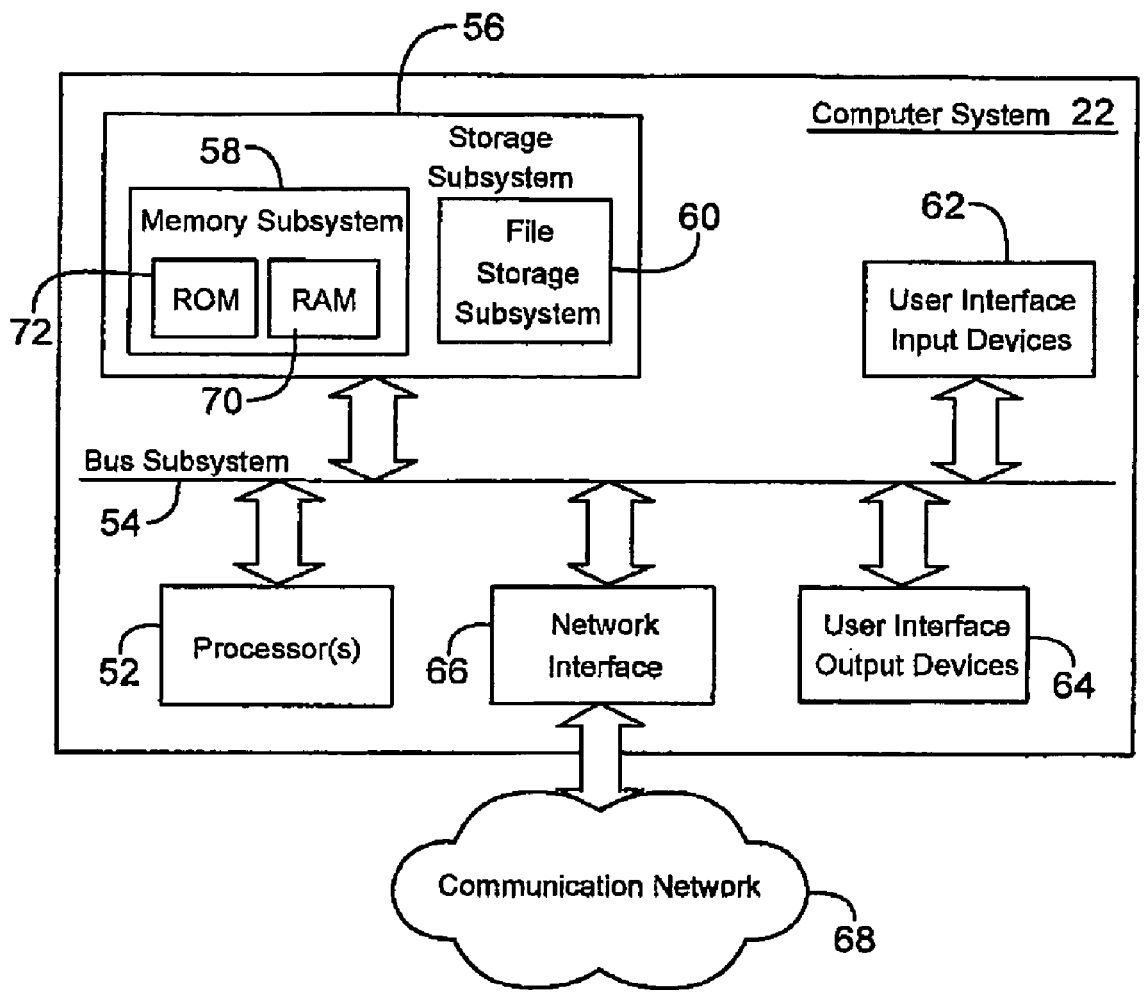
FIG. 2A is a schematic illustration showing a block diagram of a computer of the systems of FIGS. 1 and/or 2.

FIG. 2A is a simplified block diagram of an exemplary computer system 22 that may be used by the laser surgical system 10 of the present invention, and/or which may perform some or all of the method steps of effective power curve generator 4. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touch-screen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 stores the basic programming and data constructs that provide the functionality of the various embodiments of the present invention. For example, a database and modules generally comprise machine readable code, and implementing the functionality of one or more of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any of a wide variety of other data processing system. Due to the ever-changing nature of computers and networks, the description of computer system 22 depicted in FIG. 2A is intended only as a specific example for purposes of illustrating one embodiment of the present invention. Many other configurations of computer system 22 are possible having more or less components than the computer system depicted in FIG. 2A.

Figure 3:
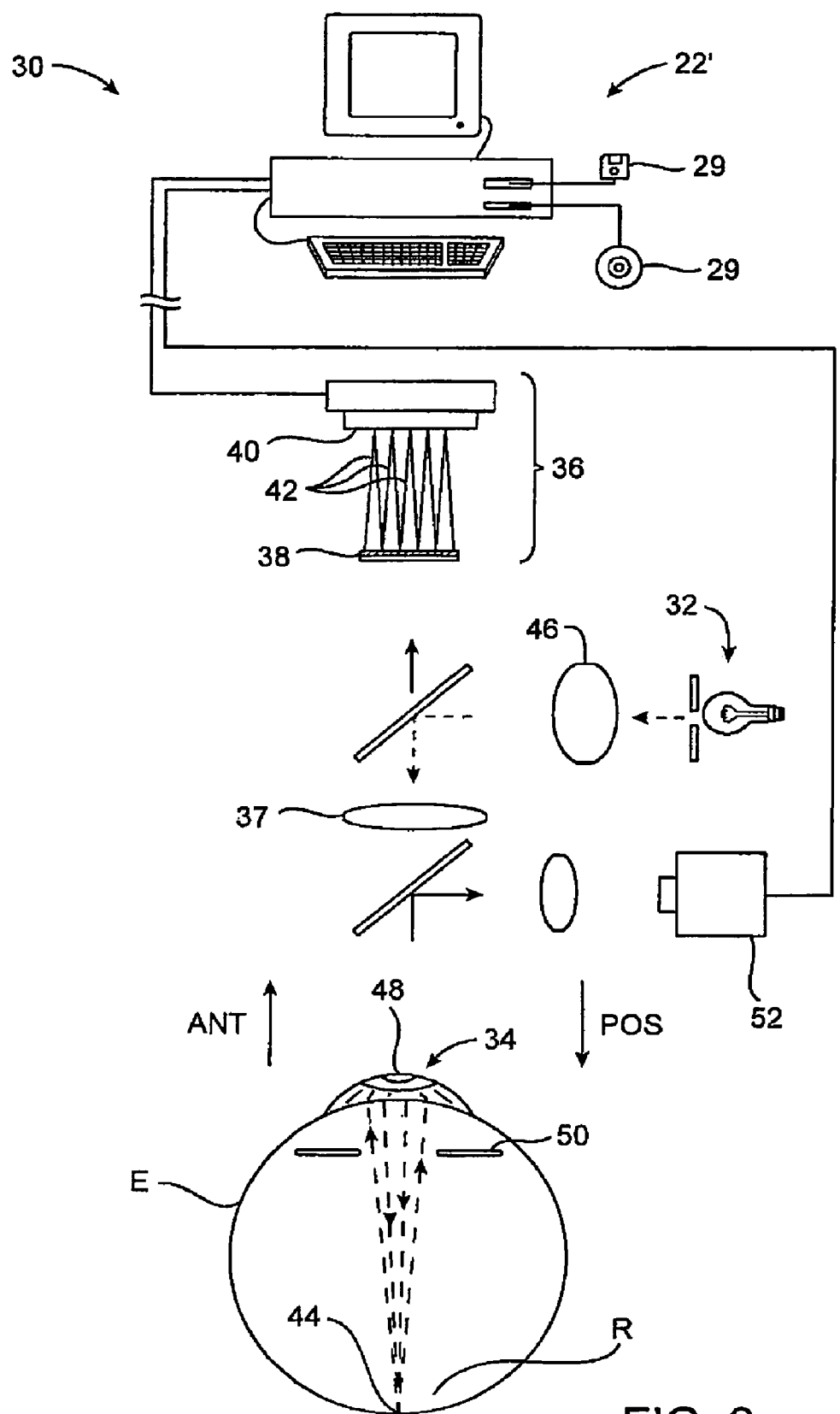
FIG. 3 is a schematic illustration showing a wavefront sensor system for measuring refractive aberrations of the eye, for use in the system of FIG. 1.

Referring now to FIG. 3, one embodiment of a wavefront measurement system 30 is schematically illustrated in simplified form, and may be used as wavefront sensor 6 (see FIG. 1). In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map. Hence, wavefront measurement system 20 may allow presbyopia system 10 to measure and/or correct irregular and/or regular refractive errors of the eye by appropriate modifications to a refractive prescription.

More specifically, wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10 and/or which generates a desired power curve, or some or all of the components of computer system 22, 22' of the wavefront measurement system 30, laser surgery system 10, and power curve generator 4 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optics system, such as a deformable mirror. Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R. The wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information may contain the available information on the wavefront error of the eye and may be sufficient to reconstruct the wavefront or any portion of it. The wavefront data may be stored in a memory of the wavefront sensor system in a single array or multiple arrays.

While some methods of the present invention may be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 4:
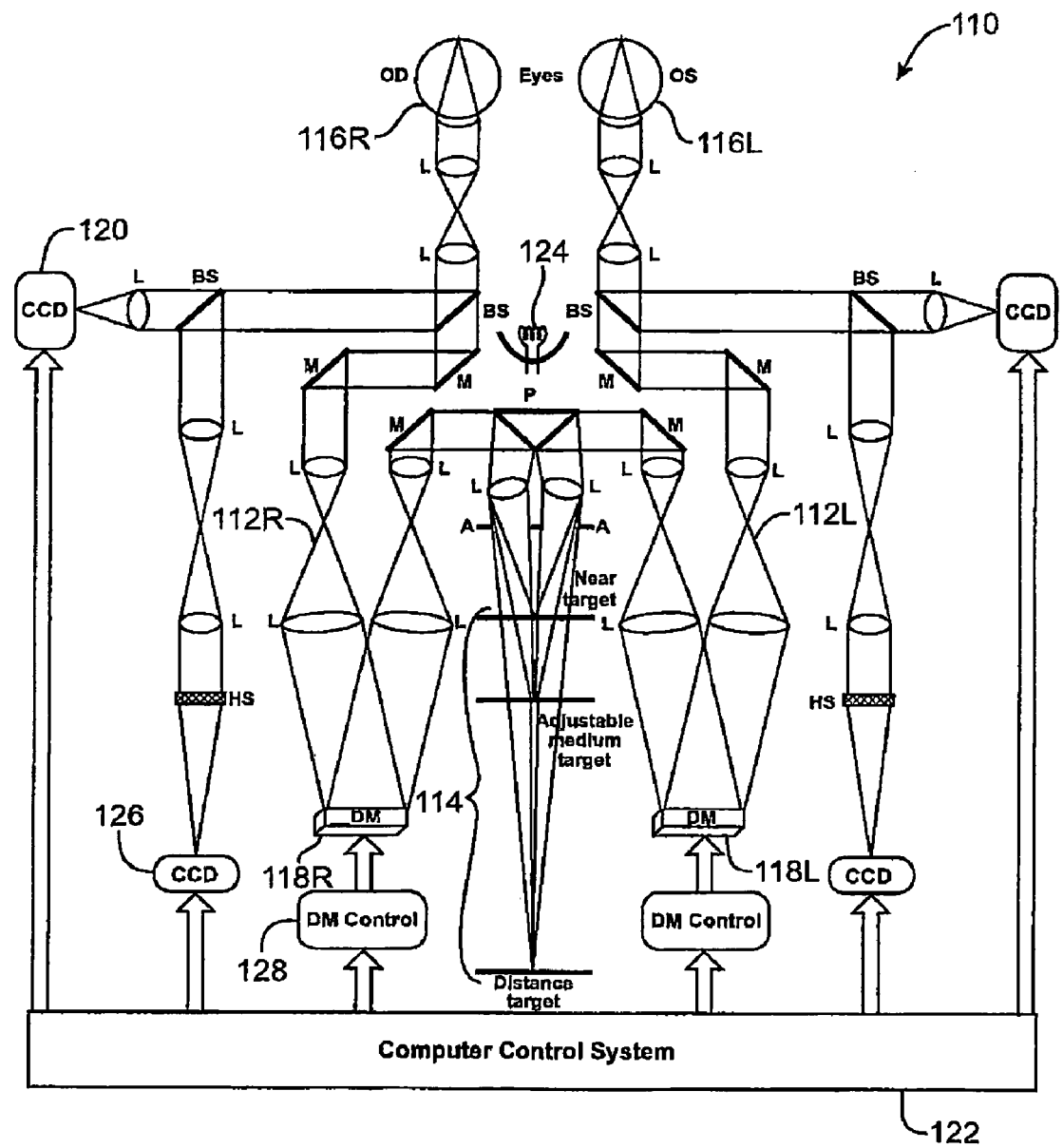
FIG. 4 is a schematic diagram of a system for measuring a response to varying viewing distances for use in the system of FIG. 1.

An exemplary variable viewing distance pupilometer 8 (see FIG. 1) with an integrated wavefront sensor is illustrated in FIG. 4. Pupilometer/wavefront sensor apparatus 110 generally includes an optical path 112R coupling an adjustable viewing distance target 114 with a right eye 166R of a patient. A similar optical path 112L couples adjustable target 114 with a left eye 116L, thereby providing a binocular viewing system. As the components of the optical path, sensors, and the like of apparatus 110 along with the right optical path 112R are generally similar to those of the left optical path 112L, only the right side need be described to understand the structure and use of the apparatus.

Optical path 112R includes a series of lenses L and mirrors M optically coupling adjustable target 114 to right eye 116R via a deformable mirror 118R. A Hartmann-Shack wavefront sensor HS is coupled to optical path 112R by a beam splitter BS for measurement of aberrations of eye 116R. A sensor 120 is also coupled to the optical path 112R by one or more beam splitters BS for measurement of a size of a pupil of eye 116R, and may also be used to determine a position of the eye and the like, as described above regarding the wavefront measurement system of FIG. 3.

Adjustable target 114 transmits an image along optical path 112R, with the light being profiled by an aperture A having a field stop, the light then being collimated by an adjustable focal-length lens L before being directed along the optical path using a prism P. At the end of the optical path adjacent eye 116R, the light is re-collimated by lenses L to go through the optics of the eye, primarily the cornea and the lens of the eye, so as to form an image on the retina.

As described above regarding the wavefront sensor of FIG. 3, light from the retina may be imaged back through the ocular optics and adjacent Lenses of optical path 112R. This light image may be split from the optical path of the target image by a Beam Splitter. This retinal image light may again be split into two channels by a second Beam Splitter. These two channels may be directed by a lens L to sensor 120 for imaging the pupil, the sensor often comprising a charge couple device ("CCD"), a pupilometer, and/or the like. The second channel may be directed from the second beam splitter BS via adjacent lenses L to a Hartmann-Shack wavefront sensor HS and its associated CCD 126. A deformable mirror control 128 and computer control system 122 of pupilometer/wavefront sensor 110 may decrease any distortion of the image formed on the back of the retina by the adjustable viewing target 114, and/or may model a presbyopia-mitigating refractive shape as more fully described in co-pending U.S. patent application Ser. No. 10/872,331, filed on Jun. 17, 2004, and entitled "Correction of Presbyopia Using Adaptive Optics and Associated Methods," the full disclosure of which is incorporated herein by reference. Apertures A, prisms P, and other components of the adjustable viewing target 114 are also more fully described in that reference, along with components of optical paths 112R and 112L. By determining the range at which eyes 116R and 116L are able to accurately image a viewing target, and optionally by measuring the changes in the wavefront from the eyes during accommodative viewing of differing viewing targets, apparatus 110 may allow measurements of residual accommodation, along with pupil size (using CCD 120), the accommodative trajectory, and the like throughout a range of viewing distances.

While it may for some patients and/or patient groups (such as hyperopes) the refractive prescription may not necessarily follow the accommodative trajectory of the eye for many patients. Instead, the desired defective power curve generator 4 will often generate a desired power curve which differs from the total accommodative trajectory of the eye so as to take advantage of any residual accommodation. More specifically, the change in effective power of the refractive prescription with a change in pupil size may be less for the desired effective power curve than for the total accommodation trajectory, as any ability of the lens L of the eye to change in shape with residual accommodation may help make up for the difference between the desired power curve and the total accommodative trajectory. The desired power curve may also differ from the accommodative trajectory due to psychophysics, a modified tissue response to imaging stimuli (such as through training the eye to alter the constriction with changes in viewing distances, training of the neural image processing capabilities of the vision system to interpret images generated by an aspherical optical system, and/or the like), latent hype rope-alike accommodation, and/or the like. Hence, desired effective power curve generator 4 may determine a relationship between accommodative power and pupil size, and may derive the desired effective power curve for a refractive prescription by modifying that relationship.

Figure 5:
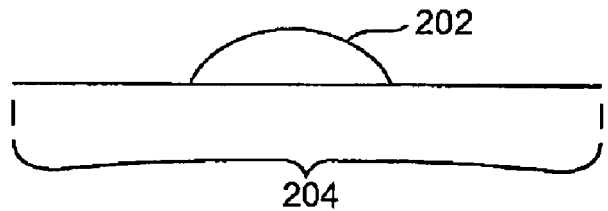
FIGS. 5 and 6 are a side view and a perspective view, respectively, of a basic refractive shape which can be scaled or modified to provide a desired effective power profile and/or to induce a desirable visual system response so as to mitigate presbyopia using the system of FIG. 1.
Figure 6:

Referring now to FIGS. 5 and 6, an exemplary aspheric presbyopic prescriptive lens basis shape 202 is shown in a simplified cross-section view and a perspective view, respectively. Presbyopic shape 202 include a central spherical portion surrounded by a peripheral plano P region, which together define an overall aspheric shape. The asphericity can be implemented by applying, for example, a laser ablation similar to that applied for treatment of hyperopia within the central region of the eye, along with a plano P ablation pattern around the central region. The size of the central region may be scaled with a pupil dimension, in an exemplary embodiment by sizing the central region at 0.48 times a size of a scotopic pupil 204, with the central portion having a power of −2.5 D. As the presbyopic power of the central region is smaller than a pupil diameter, a substantial portion of the total area (as much as 77% in the exemplary embodiment) does not have any additional spherical power. Theoretical analysis and data comparisons of a model representing the small spherical central shape indicates that its contribution to the power of the overall optics within the pupil aperture can be assessed to calculate the effective power of this aspherical shape on the overall refractive optics of the eye.

Effective power is the dioptric power one sees through a set of optics. Manifest refraction is an operational measure of effective power. For a spherical correction, manifest refraction does not change with changes in pupil diameter. In contrast, an aspheric correction can change in manifest refraction with changes in pupil diameter. Hence, the asphericity can effect the manifest measurements, in that manifest refractions may be different with different pupil diameters.

An analysis of asphericity may involve evaluating the effective power of an aspheric shape. This evaluation may involve calculating the spherical power of the aspherical shape within a range of differing pupil diameters, often at a plurality of pupil diameters within the range. Optionally, power may be evaluated continuously throughout the range. To calculate effective power, aspherical shapes may be decomposed into their Zernike expansion. Effective power may then be calculated with the following formula:

$$EffectivePower = -4\left(\frac{\sqrt{3}c_4}{r^2}\right) + 2\left(\frac{\sqrt{6}\sqrt{c_3^2 + c_5^2}}{r^2}\right)$$

In this equation, $c_3$, $c_4$, and $C_5$, are the standard OSA indexed Zernike coefficients, and r is the pupil radius.

Applying the above equation to the exemplary presbyopia shape of FIGS. 5 and 6, the Zernike expansion of that shape with a 6 mm pupil size using the OSA convention would be $S_{6mm} = 0.327428Z_4 - 0.30046Z_{12} + 0.003138Z_{14} + 0.201588Z_{24} + 0.003462Z_{26}$ Inserting the Zernike coefficients for this shape into the equation for calculating effective indicates that the effective power for this shape with a 6 mm pupil is:

$$EffectivePower = -4\sqrt{3}\,\frac{0.327428}{3^2}$$
$$= -0.252 \text{ Diopters}$$

Figure 7:
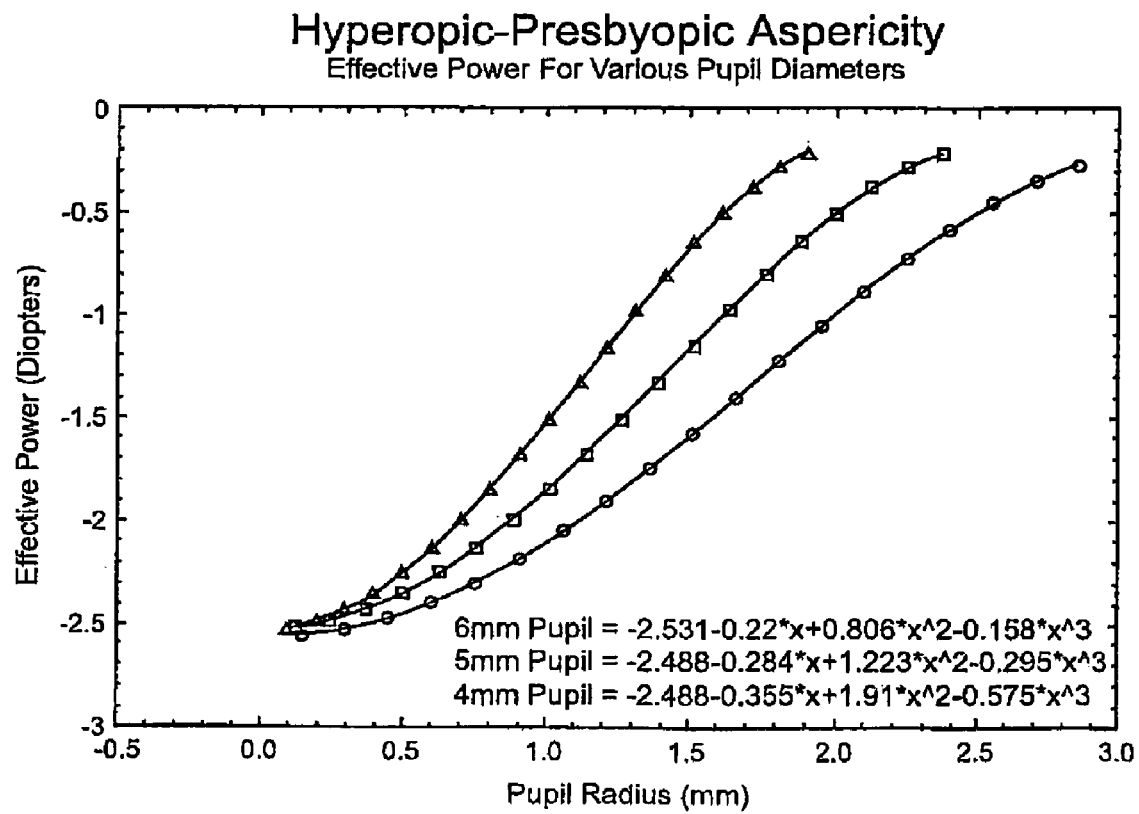
FIG. 7 graphically illustrates changes in effective power with changes in pupil size using the refractive shape of FIGS. 5A and 5B so as to provide pseudo accommodation.

Hence, this exemplary presbyopic shape produces a myopic shift of about −0.25 D. The effective power for this lens at a range of different pupil diameters were also calculated from the Zernike expansions of the associated surfaces by a method described by Jim Schweigerling entitled "Scaling Zernike Expansion Coefficients to Different Pupil Sizes," *J. Opt. Soc. Am.*, Vol. 19, No. 10, Oct. 2002, pp. 1937-45, and the results are graphically illustrated in FIG. 7. The three curves in the graph show the changes in effective power with constriction of the pupil for the above-described shape scaled for a 6 millimeter pupil size. Curves are also shown with the central portion scaled for a 5 mm pupil size and a 4 mm pupil size, the pupil sizes being again being for the scotopic pupil. The smooth lines are third order curves fit to the calculated values, and the equations for these curves are:

6 mm Pupil=−2.531−0.22*x+0.806*x^2−0.158*x^3

5 mm Pupil=−2.488−0.284*x+1.223*x^2−0.295*x^3

4 mm Pupil=−2.488−0.355*x+1.91*x^2−0.575*x^3

A wide variety of alternative curve equation formats may also be employed.

Figure 8:
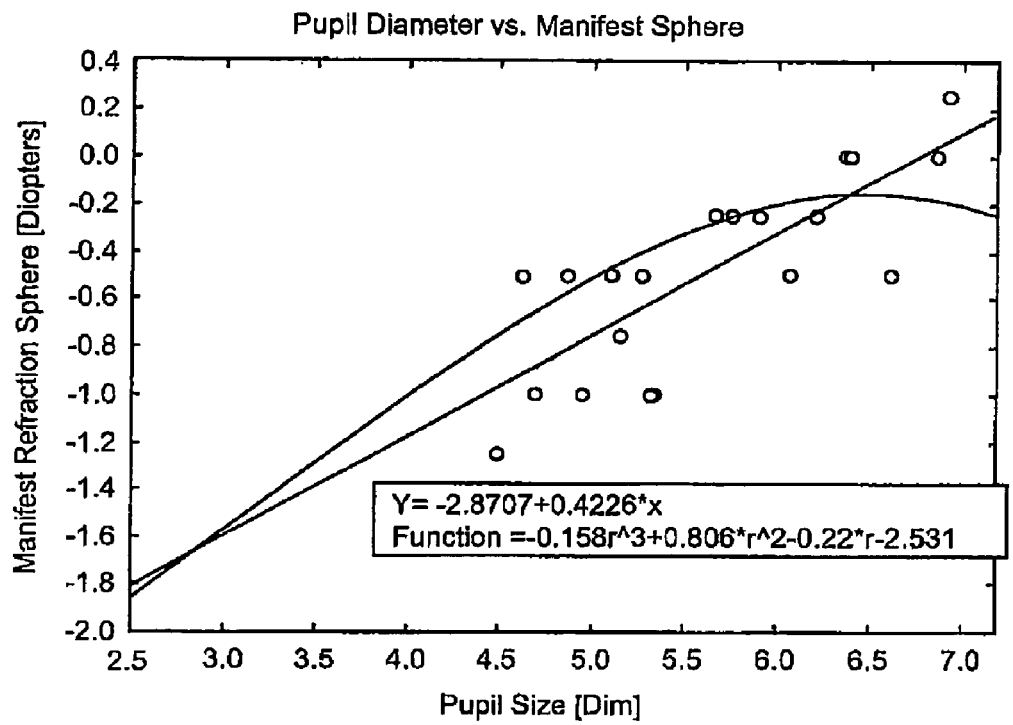
FIG. 8 graphically illustrates clinical data indicating a relationship between manifest spherical power and pupil size for a number of different patients.

Referring now to FIG. 8, clinical data from one or more prior patients may be used to help determine a total accommodative trajectory. FIG. 8 shows data from twenty eyes treated using laser eye surgery. Each of the eyes had the ablation profile illustrated in FIGS. 5 and 6 imposed on the eye, with the size of the central portion being consistently 2.5 mm in diameter regardless of the pupil size of the eyes.

Manifest redaction sphere powers of the eyes were measured, and plotted against the measured pupil size. A linear equation fit to the data indicates that the rate of power change is about 0.4 D per millimeter of pupil diameter.

From the above discussion regarding changes in optical power with constriction of the pupil, the manifest power should correlate with the aspheric change in effective power of our model. The curved line shown in FIG. 8 represents a theoretical 7.2 mm pupil treated with the same 2.5 mm central portion presbyopia shape that was imposed on the twenty eyes, giving a central portion to pupil ratio of 0.34. As indicated in FIG. 8, the curved theoretical line correlates well with the clinical results. Hence, manifest refraction sphere of an individual patient, as that patient's pupil constricts appears to provide an effective power variation that correlates to clinical data from a plurality of different patients, and the effective power model appears reasonable.

It may be advantageous to customize the presbyopia shape for a particular patient by measuring the accommodative power requirement and the corresponding pupil size for that patient. From this information, a shape may be generated which produces the desired accommodative trajectory. As a result, changes in the pupil size during accommodation will induce changes in the effective power of the refractive tissue, thereby simulating natural accommodation. There may, however, be disadvantages in highly aspheric lenses that are capable of generating large changes in effective power so as to fully simulate the accommodative trajectory. For example, highly aspheric lens shapes may degrade visual acuity at one or more viewing distances, such as at a far viewing distance, a near viewing distance, or one or more intermediate viewing distances. Additionally, it may be difficult to provide a refractive prescription which exactly compensates for the accommodative trajectory, and/or the accommodative trajectory may change with increasing age, differing lighting conditions, fatigue of the eye or patient, and/or the like. Advantageously, residual accommodation may aid the patient's visual system performance when the accommodative trajectory and effective power of the refractive prescription differ.

Figure 9:
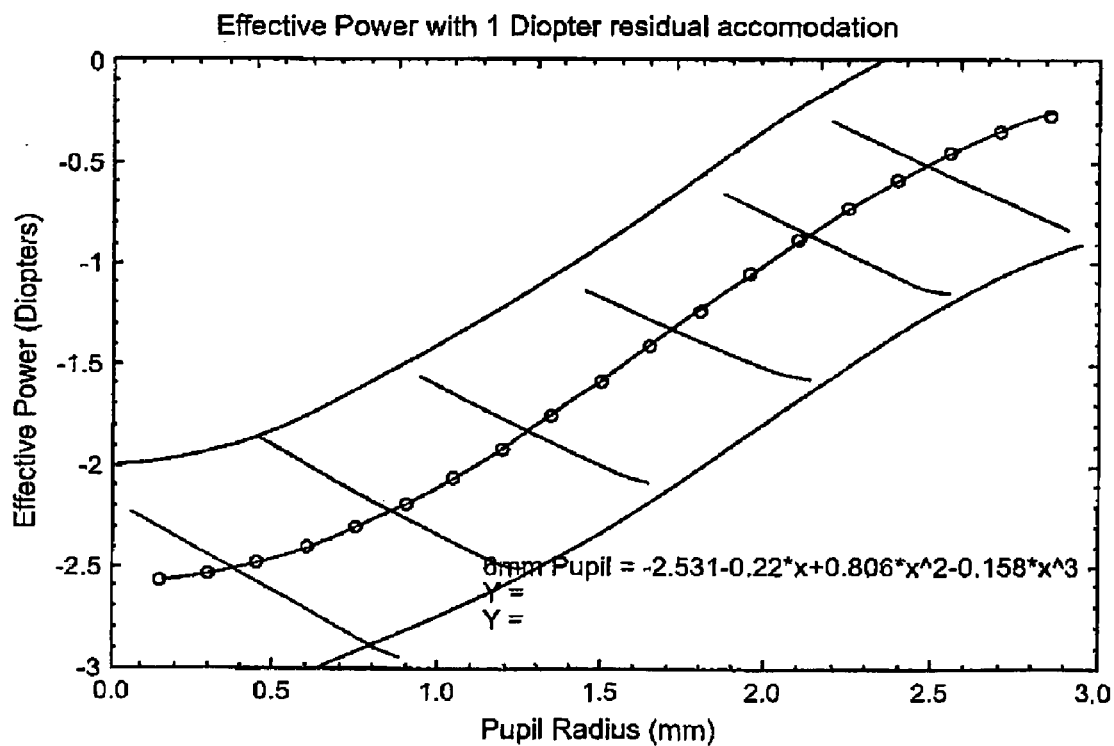
FIG. 9 graphically illustrates the effects of residual accommodation on an effective power/pupil size curve.

Referring now to FIG. 9, residual accommodation may, for example, allow a patient to exhibit good visual acuity despite a presbyopic shape which presents an imperfect fit to the accommodative trajectory. In this example, an eye having one diopter of residual accommodation may allow the patient to image with good acuity anywhere throughout a one-diopter visual accommodation range, effectively indicating the power to pupil diameter curve may be a one-diopter thick line, band, or range, rather than a thin theoretical line as indicated above. The desired power curve from which the refractive prescription is generated will, nonetheless, typically comprise such a thin theoretical curve, and will typically be disposed at least in part within the range or band of residual accommodation, often being primarily disposed within the band of residual accommodation, and ideally being contained within the band of residual accommodation. Preferably, the prescriptive shape will have properties which allow the eye to adjust so as to take advantage of its optical properties so as to provide good visual acuity throughout a range of viewing distances. In some embodiments, the visual system may benefit from training so as to take full advantage of the prescription.

Figure 10A:
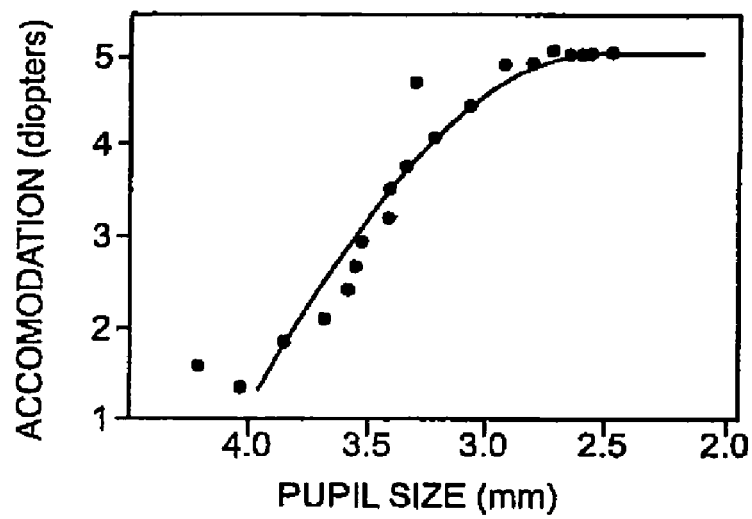
Figure 10B:
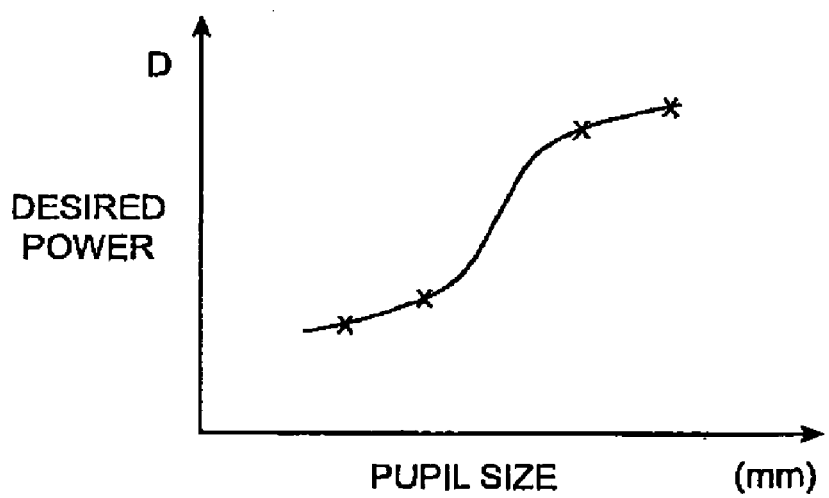

Referring now to FIG. 1A, a relationship between accommodation and pupil size in healthy eyes allows those eyes to adjust to differing viewing distances. As illustrated in FIG. 10B, an appropriate relationship between effective power of an eye and pupil size for a particular patient can be provided from a refractive presbyopia prescription so as to effect desired changes in power with changes in pupil size under differing viewing conditions. The aspheric shape described above (having a spherical central region and a planar peripheral region) is one example of a shape which may be modified, tailored, changed in size, power, and/or the like so as to provide a desired relationship between effective power and pupil size. Other shapes are described in more detail in co-pending U.S. patent application Ser. No. 10/738,358, entitled "Presbyopia Correction Using Patient Data," as filed on Dec. 5, 2003, the full disclosure of which has been incorporated herein by reference, which also describes methods for the calculation of such shapes. Suitable shapes may be generated by optimization routines so as to optimize an appropriate visual performance metric at a plurality of viewing distances or a range of viewing distances, by matching an effective power requirement at a plurality of points or throughout a range, or the like. Regardless, the desired power versus pupil size data may be measured directly for the patient for whom the prescription is to be derived. Alternatively, as illustrated in FIG. 1C, a relationship between manifest power and pupil diameter may be measured from a plurality of prior patients having differing pupil diameters and who have been successfully treated with a presbyopia-mitigating prescription. The relationship may then be use to identify the desired change in optical power with changes in pupil diameter for a specific patient, as described above.

Figure 11:
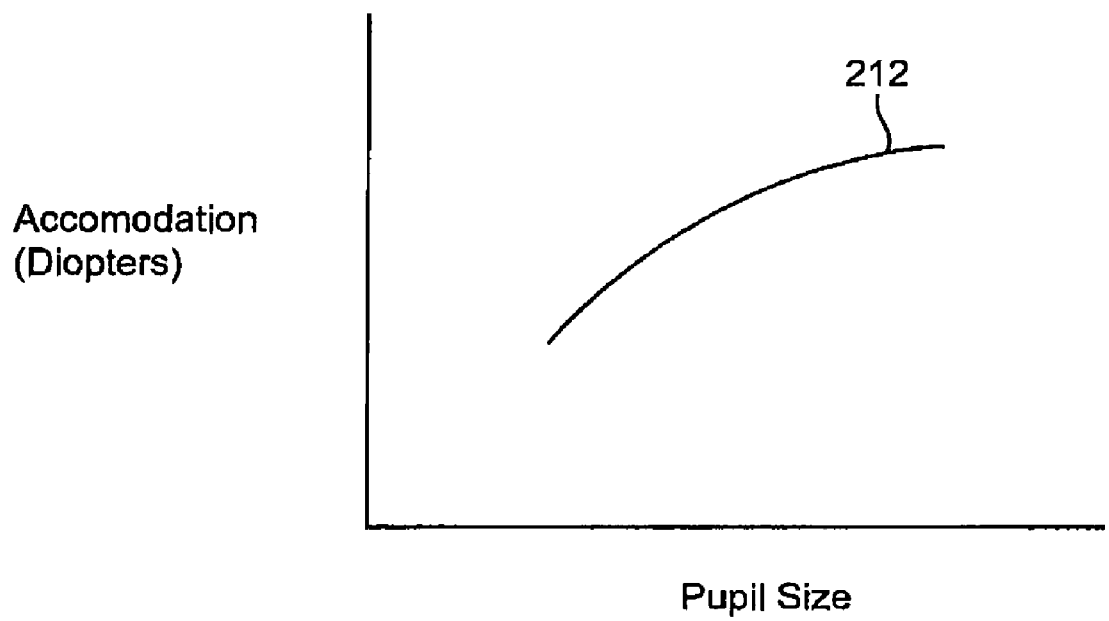
FIG. 11 graphically illustrates a schematic relationship between accommodation and pupil size.

Referring now to FIG. 11, using one or more of the methods described herein, or using any other suitable method, a relationship 212 between total accommodative power and pupil size for the patient may be developed, the relationship typically comprising the accommodative trajectory. Relationship 212 indicates a total optical presbyopia compensation power with changes in pupil size. Relationship 212 has a rate of change in power for changes in pupil size which may be constant through some or all of the pupil size variation range, or may have a rate which changes as shown in FIG. 11.

Figure 12:
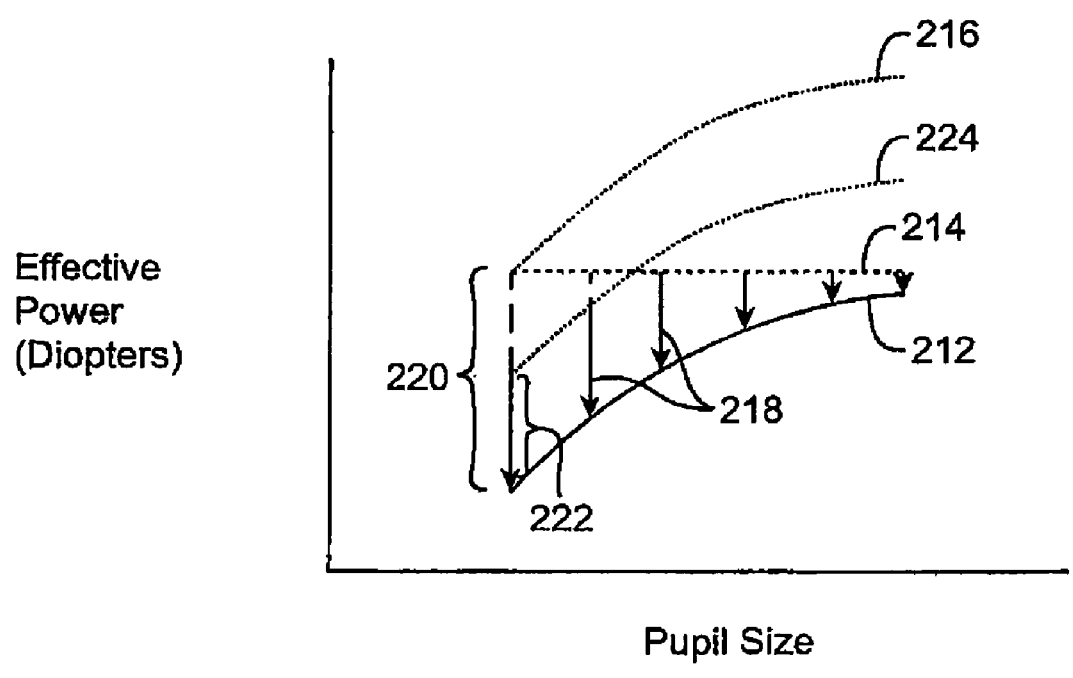
FIG. 12 graphically illustrates a relationship between effective power and pupil size for a latent hyperope, and shows how such individuals accommodate at different viewing distances.

Referring now to FIG. 12, a theoretical graph schematically illustrates how hyperopic eyes adjust to changes in viewing distances. A cornea 214 is here shown as having a spherical shape, so that its power does not change with changes in pupil size. For a latent hyperope having a sufficient residual accommodation band limit 216, the eye fully adjusts or accommodates as the patient views at differing viewing conditions. More specifically, along with changes in the pupil size, the lens of the eye changes shape to drive the overall power of the eye down 218 as needed to provide the overall accommodative trajectory relationship 212. So long as the eye retains sufficient residual accommodation 220, the patient remains a latent hyperope with good visual acuity throughout the range of viewing distances (despite a latent spherical error in the refractive properties of the eye). However, as accommodation decreases with age to a smaller residual accommodation 222, the band of acceptable effective power of the eye decreases to the range between the line at 212 and the reduced residual accommodation limit 224. As the patient is no longer capable of accommodating throughout the range of viewing distances, when viewing at a near distance the residual accommodation is insufficient to provide the relationship 212 due to the excessive power of the cornea 214. Hence, the patient is no loner a latent hyperope and is now hyperopic.

Figure 13:
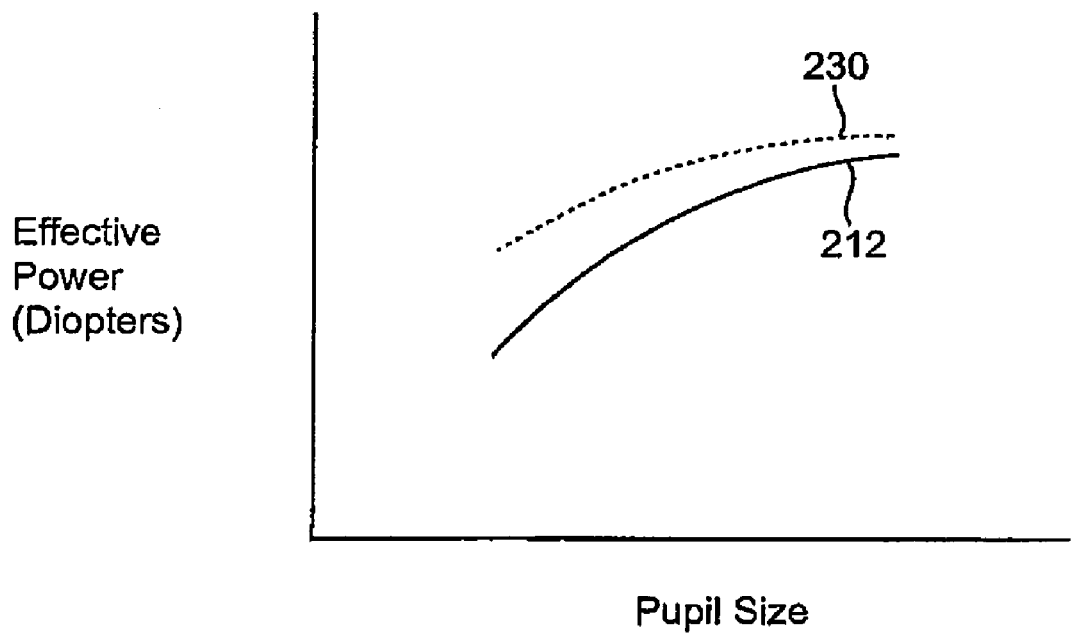
FIG. 13 schematically illustrates a desired effective power curve having a slope that is less than a total accommodation power curve so as to fully compensate for changes in viewing distance with changes in pupil size, and which may induce a tissue response so as to mitigate presbyopia.
Figure 13A:
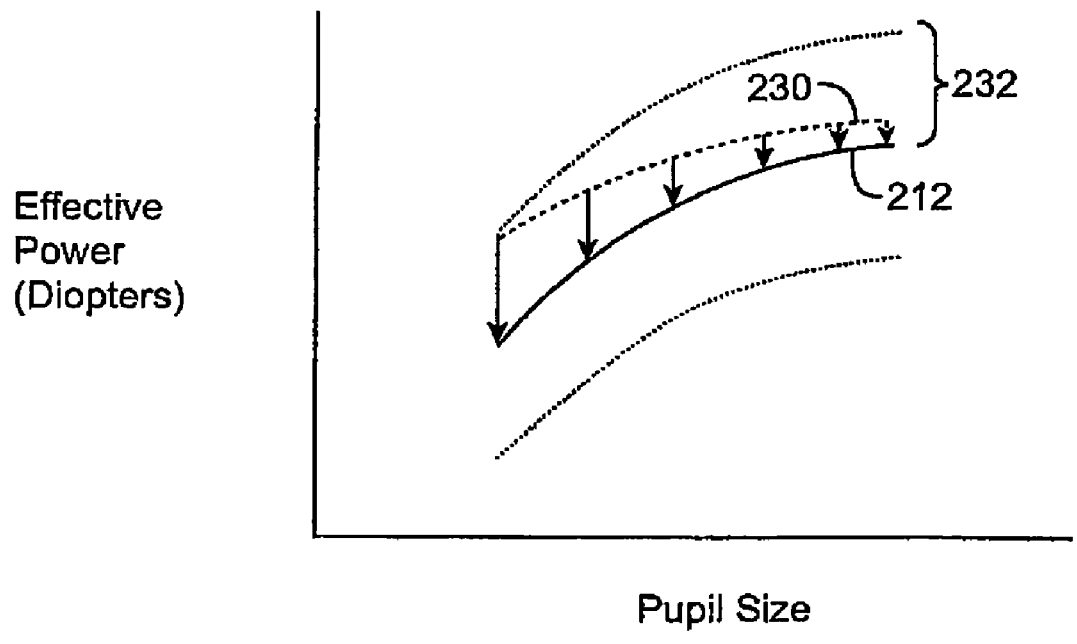
FIG. 13A schematically illustrates a trained latent hyperope-like accommodation tissue response in combination with changes in effective power of an aspherical shape so as to mitigate presbyopia using a patient's residual accommodation.

By taking advantage of accommodation similar to that of a latent hyperope, and by designing an appropriate effective power curve 230, a patient may take advantage of their residual accommodation throughout a range of viewing distances, as indicated by FIGS. 13 and 13A. Note that desired power curve 230 has a rate of change in effective power which is less than the total optical compensation power indicated by accommodative trajectory 212. Nonetheless, so long as the power curve 230 remains within a residual accommodation band 232, the patient can make use of their residual accommodation to obtain the desired image quality using an accommodative approach similar to that of a latent hyperope. Even where a desired effective power curve 230 extends outside the accommodative band 232, the residual accommodation may still provide acceptable (if not ideal) imaging, and/or the power of any viewing aid such as reading glasses or the like may be decreased.

As the accommodation effected using a refractive prescription generated from desired power curve 230 is similar to that of a latent hyperope, patients who were latent or actual hyperopes may find it easier to take advantage of the refractive prescription, thereby providing visual performance for those patients quite soon after the prescription is applied to the eye. Other patients, such as emmetropic presbyopes or patients who are simultaneously being treated for presbyopia with myopia, astigmatism, and/or irregular aberrations of the refractive tissues, may benefit from more extended training of the visual system. The training may simply comprise the gradual learning that occurs naturally as the eye views images after the prescription is imposed. Surprisingly, such training may extend for a significant amount of time even after the optical tissues have substantially stabilized, so that visual acuities at one or more viewing distances and/or patient satisfaction may increase after more than one hour, after more than one day, after more than one week, and even after more than one month. In other words, a myopic presbyope treated with a refractive shape providing the desired effective power curve 230 within accommodation band 232 may have an increase in their measurable visual acuity at near (and/or far) viewing distances, an increase in their satisfaction, or the like, beyond a baseline measured one month after a refractive laser procedure. When tested again at, for example, three months after the procedure such a patient will often have shown significant improvement in near viewing. So as to improve initial satisfaction, accommodative eye exercises may be employed, a removably contact or scleral lens may be temporarily fitted to the eye, or the like.

Figure 14:
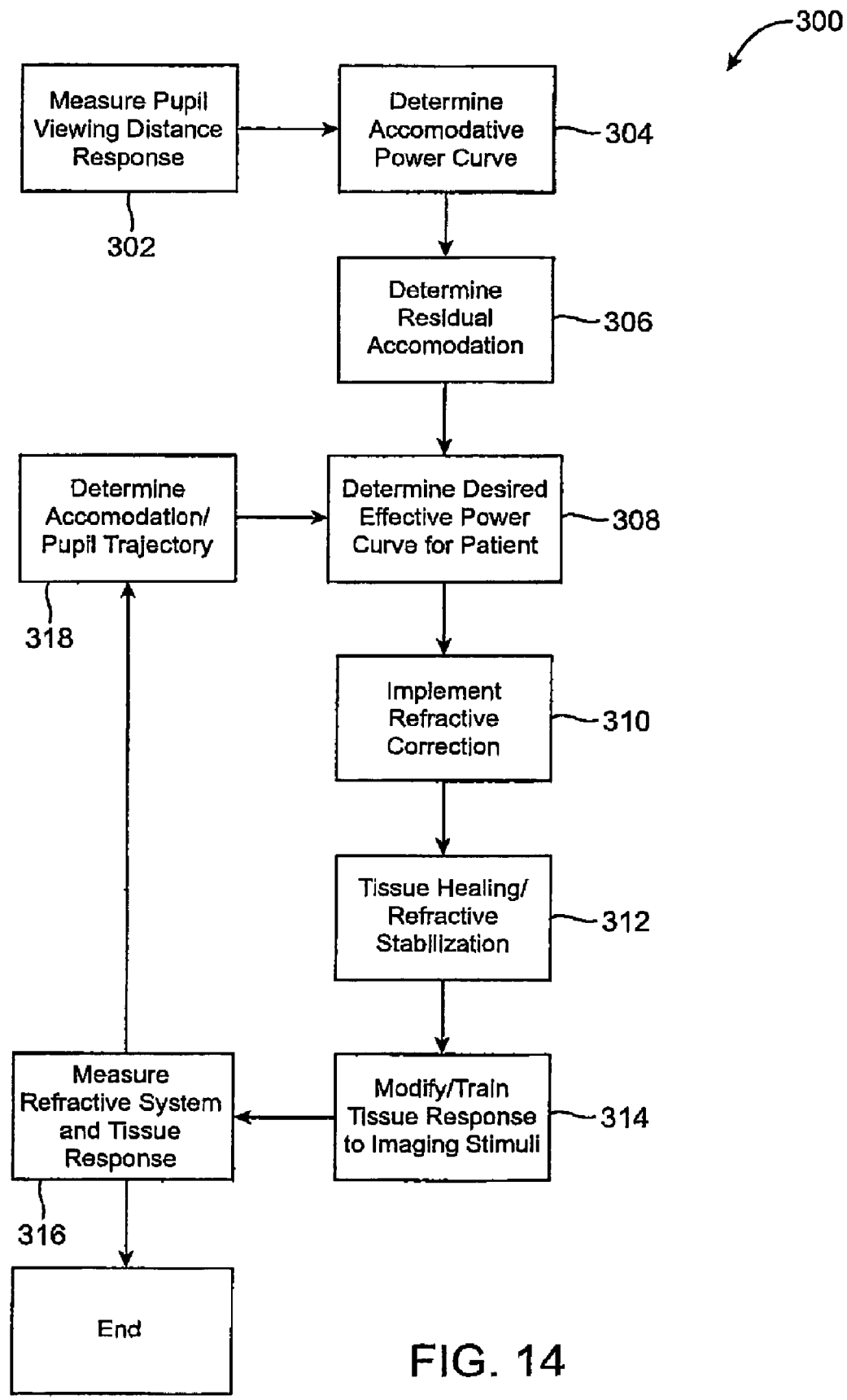
FIG. 14 is a schematic flow chart illustrating a method for determining a prescription for and treating of a patient having presbyopia.

Referring now to FIG. 14, a method for treating presbyopia 300 in a visual system of a patient will often comprise measuring viewing distance response of the pupil 302. Optionally an integrated wavefront/pupilometer apparatus 110 such as that shown in FIG. 4 may be used, or any other variable viewing distance pupilometer system may be employed. Wavefront sensor data will often be taken as well, optionally using a wavefront sensor such as that shown in FIG. 3. Any other commercially available wavefront or other aberrometer system may alternatively be used. The use of such wavefront data for correcting any aberrations of the eye is well described in the patent literature, and may be readily combined with the presbyopia treatments described herein.

The next step in presbyopia treatment method 300 is optionally to determine an accommodative power curve 304 or accommodative trajectory as described above. Residual accommodation 306 can be determined by measuring the viewing range of the patient, by wavefront sensor measurements using apparatus 110 of FIG. 4, or by any other desired method. The desired effective power curve for the patient can be determined 308 from the residual accommodation and/or accommodative power curve as described above, or the desired effective power curve may alternatively be determined more directly from the viewing distance response or the like. Regardless, the refractive correction is implemented 310 on the patient, either temporarily or permanently.

Optionally, the refractive correction may be implemented by laser ablation of selective corneal tissue using a laser ablation system similar to that described with reference to FIG. 2. In alternative embodiments, a laser system may selectively ablate material from a contact lens, a scleral lens, an intraocular lens, or the like, or these lenses may otherwise be fabricated or modified so as to have a refractive correction with a suitable effective power curve.

When the desired refractive correction is permanently imposed using a laser system or the like, a tissue healing and refractive stabilization process 312 may occupy at least some time after the refractive correction treatment. In LASIK procedures and the like, optical stabilization can occur quite quickly. In other procedures, possibly including photorefractive keratectomy ("PRK"), refractive tissue stabilization may take some time, for example, with full epithelial tissue growth taking one week or more.

Separate from the tissue healing/refractive stabilization step 312, there may also be a modification or training of a tissue response to imaging stimuli 314 if the patient is to take full advantage of the presbyopic mitigation available by the refractive procedure. This tissue response training may be quite quick for some subgroups of patients, and may extend for a more significant period of time for at least some other patients. In some embodiments, modification or training of the tissue response may extend significantly past the optical or refractive tissue stabilization 312. Hence, patient satisfaction and at least one of near or far visual acuity (often being near visual acuity) may undergo significant improvements after refractive tissue stabilization (optionally being more than one hour, one day, one week, or even one month after the procedure is completed). In other embodiments, it may be possible to begin modification or training of the tissue response prior to permanent imposition of a refractive correction using contact lenses or the like.

In many embodiments, the refractive system and tissue response will be measured 316. An accommodative trajectory may be determined 318, and the desired effective power curves for future patients may make use of that clinical experience. In other embodiments, particularly when a temporary refractive correction such as a contact lens or the like has been used, the accommodative trajectory for a patient with the refractive correction may be used to derive or determine a new desired effective power curve for that patient.

While the exemplary embodiments or devices, methods, and systems of the present invention have been described in some detail by way of example and for clarity of understanding, a variety of modifications, changes, and adaptations will be obvious to those with skill in the art. Hence, the scope of the invention is limited solely by the appended claims.

What is claimed is:

1. A method for treating presbyopia in a visual system of a patient, the visual system including an eye, the method comprising:

applying a refractive prescriptive change to the eye, the refractive change altering optical properties of the eye so as to provide a first near acuity and a first far acuity; and in response to the altered optical properties of the eye, inducing a modified response of the visual system by training the visual system so as to provide:

a second near acuity better than the first near acuity, or a second far acuity better than the first far acuity;

such that presbyopia of the eye is mitigated.

2. The method of claim 1, wherein the modified response of the visual system significantly improves visual acuity from an optically stabilized acuity to a trained acuity significantly after the altered optical properties of the eye have substantially stabilized.

3. The method of claim 1, wherein the refractive prescriptive change is applied by a LASIK procedure, wherein the eye has the first near acuity at least one hour after the LASIK procedure, and wherein more than 1 hour after the LASIK procedure the modified response of the visual system measurably improves the first near acuity such that presbyopia of the eye is mitigated.

4. The method of claim 3, wherein the eye has the first near visual acuity at least one month after the LASIK procedure, and wherein more than 1 month after the LASIK procedure the modified response of the visual system measurably improves the near visual acuity such that presbyopia of the eye is mitigated.

5. The method of claim 1, wherein the modified response of the visual system comprises a modified tissue response to imaging stimuli.

6. The method of claim 1, wherein the modified response of the visual system comprises psychophysics, trained pupil pseudo-accommodation, or latent-presbyope-like accommodation.

7. The method of claim 6, wherein the modified response of the visual system is obtained by training the visual system of the patient to take advantage of the altered optical characteristics.

8. The method of claim 1, further comprising determining an anticipated visual system response, and generating the refractive prescriptive change using the anticipated visual system response.

9. The method of claim 1, wherein the anticipated visual system response corresponds to a rate of change in effective power of the eye with changes in pupil size, the rate being equal to or lower than an optical presbyopia compensation rate.

10. The method of claim 1, further comprising determining the refractive prescriptive change based on trained pupil responses of eyes of prior patients, the trained pupil responses being different than pupil responses before training.

11. The method of claim 1, wherein the refractive prescriptive change treats myopia of the eye of the patient, further comprising determining the refractive prescriptive change based on accommodation of latent hyperopes, and wherein the modified response mitigates the presbyopia by employing residual accommodation of the eye of the patient per latent hyperope accommodation.

12. A method for treating presbyopia in a visual system of a patient, the visual system including an eye, the method comprising:
    determining an anticipated visual system response, and generating a refractive prescriptive change using the anticipated visual system response, wherein the anticipated visual system response is determined by studying visual system responses of prior patients, and wherein the anticipated visual system response corresponds to a rate of change in effective power of the eye with changes in pupil size, the rate being lower than an optical presbyopia compensation rate;
    applying the refractive prescriptive change to the eye, the refractive change altering optical properties of the eye so as to provide a first near acuity and a first far acuity; and
    and in response to the altered optical properties of the eye, inducing a modified tissue response of the visual system so as to provide:
        a second near acuity better than the first near acuity, or
        a second far acuity better than the first far acuity;
        such that presbyopia of the eye is mitigated.

13. The method of claim 12, further comprising tailoring the refractive prescription using a measured response of the patient, the measured response comprising at least one of a pupil dilation response and residual accommodation.

14. The method of claim 12, wherein the anticipated visual system response corresponds to a rate of change in effective power of the eye with changes in the pupil size, the rate being within the anticipated residual accommodation range.

15. A method for treating presbyopia in a visual system of a patient, the visual system including an eye, the method comprising:
    determining an anticipated visual system response, and generating a refractive prescriptive change using the anticipated visual system response;
    applying the refractive prescriptive change to the eye, the refractive change altering optical properties of the eye so as to provide a first near acuity and a first far acuity; and
    in response to the altered optical properties of the eye, inducing a modified response of the visual system so as to provide:
        a second near acuity better than the first near acuity, or
        a second far acuity better than the first far acuity;
        such that presbyopia of the eye is mitigated;
    wherein the anticipated visual system response corresponds to a change in effective power with changes in pupil size at an anticipated rate of between about 0.4 D per mm and about 0.6 D per mm, and a change in manifest power with a change in pupil size is greater than the anticipated rate.

16. The method of claim 15, wherein the first far acuity is at least about 20/20 so that the mitigation of presbyopia is effected by improving near visual acuity after the refractive prescriptive change is imposed.

17. A system for treating presbyopia in a visual system of a patient, the visual system including an eye, the system comprising:
    a laser for resculpting the eye of the patient according to a refractive prescription,
    the prescription altering optical properties of the eye so that the eye, after optical stabilization has a first near acuity and a first far acuity; and
    a processor coupled to the laser resculpting system, the processor comprising machine-readable software embodying instructions for determining the refractive prescription from optical properties of the eye such that the altered optical properties of the eye induce a modified response of the visual system so as to provide:
        a second near acuity better than the first near acuity, or
        a second far acuity better than the first far acuity;
        such that presbyopia of the eye is mitigated.

18. The system of claim 17, wherein the processor comprises machine-readable software embodying instructions for determining the refractive prescriptive change based on trained pupil responses of eyes of prior patients, the trained pupil responses being different than pupil responses before training.

19. The system of claim 17, wherein the processor comprises machine-readable software embodying instructions for determining the refractive prescriptive change so as to treat myopia of the eye of the patient, and for determining the refractive prescriptive change based on accommodation of latent hyperopes so that the modified response of the visual system mitigates the presbyopia by employing residual accommodation of the eye of the patient per latent hyperope accommodation.

20. A system for determining a refractive prescription so as to mitigate presbyopia in a visual system of a patient, the visual system including an eye with refractive tissues, the system comprising:
an aberrometer for measuring initial optical properties of the eye; and
a processor coupled to the aberrometer, the processor comprising a machine-readable software embodying instructions for determining the refractive prescription from the initial optical properties of the eye so that the refractive tissues of the eye provide, when the eye has optically stabilized, a first near acuity and a first far acuity, the altered optical properties of the eye configured to induce a modified response of the visual system so as to provide:
a second near acuity better than the first near acuity, or a second far acuity better than the first far acuity;
such that presbyopia of the eye is mitigated.

21. The system of claim 20, wherein the processor comprises machine-readable software embodying instructions for determining the refractive prescriptive change based on trained pupil responses of eyes of prior patients, the trained pupil responses being different than pupil responses before training.

22. The system of claim 20, wherein the processor comprises machine-readable software embodying instructions for determining the refractive prescriptive change so as to treat myopia of the eye of the patient, and for determining the refractive prescriptive change based on accommodation of latent hyperopes so that the modified response of the visual system mitigates the presbyopia by employing residual accommodation of the eye of the patient per latent hyperope accommodation.

* * * * *